United States Patent
Nolan, Jr. et al.

[11] Patent Number: 5,808,203
[45] Date of Patent: Sep. 15, 1998

[54] FLUID PRESSURE MEASUREMENT DEVICES

[75] Inventors: William J. Nolan, Jr., Indianola; Kevin P. Cowan, Allison Park; Alan D. Hirschman, Pittsburgh; David M. Reilly, Glenshaw; Frederick W. Trombley, III, Gibsonia; David M. Griffiths, Pittsburgh, all of Pa.

[73] Assignee: Medrad, Inc., Indianola, Pa.

[21] Appl. No.: 854,411

[22] Filed: May 12, 1997

[51] Int. Cl.⁶ .................................. G01L 7/00; A61M 3/00
[52] U.S. Cl. ................................ 73/700; 604/67; 73/744
[58] Field of Search ............................. 73/700, 715, 717, 73/744–46, 861.11, 861.16, 862.451; 128/DIG. 1, DIG. 2; 604/65, 657

[56] References Cited

U.S. PATENT DOCUMENTS

| | | | |
|---|---|---|---|
| 4,261,208 | 4/1981 | Hok et al. | 73/753 |
| 4,492,317 | 1/1985 | Guess et al. | 73/744 |
| 4,551,133 | 11/1985 | Zagers De Beyl et al. | 604/67 X |
| 4,759,750 | 7/1988 | DeVries et al. | 73/864.16 X |
| 5,139,484 | 8/1992 | Hazon et al. | 604/65 X |
| 5,242,408 | 9/1993 | Jhuboo et al. | 604/67 X |
| 5,244,461 | 9/1993 | Derlien | 604/67 X |
| 5,270,685 | 12/1993 | Hagen et al. | 128/DIG. 12 X |
| 5,295,967 | 3/1994 | Rondelet et al. | 604/67 X |
| 5,354,273 | 10/1994 | Hagen | 604/67 X |
| 5,459,700 | 10/1995 | Jacobs | 368/10 |
| 5,460,609 | 10/1995 | O'Donnell | 604/100 |
| 5,628,309 | 5/1997 | Brown | 604/65 X |
| 5,661,245 | 8/1997 | Svoboda et al. | 73/726 X |

Primary Examiner—George M. Dombroske
Assistant Examiner—Paul D. Amrozowicz
Attorney, Agent, or Firm—Gretchen Platt Stubenvoll; Gregory L. Bradley

[57] ABSTRACT

The present invention provides pressure measuring devices comprising a sensor to detect the force upon at least a portion of a contact surface of a syringe plunger during pressurization of a fluid medium within the syringe. A determination of the pressure of the fluid medium within the syringe is thereby enabled.

19 Claims, 11 Drawing Sheets

FLUID PRESSURE MEASUREMENT DEVICES

FIELD OF THE INVENTION

The present invention relates to a pressure measuring device for use in an injection system, an injection system comprising such a pressure measurement device, and a method for measuring pressure in an injection system, and, particularly, to such a pressure measurement device, injection system and method for use in connection with injecting a fluid medium into a patient.

BACKGROUND OF THE INVENTION

A number of injectors and syringes for use in medical procedures such as angiography, computer tomography and NMR/MRI have been developed. In such applications there is a need to measure the pressure of the fluid being injected into a patient, with some applications requiring a more accurate measurement than others. In current syringe injection devices, fluid pressure is generally measured indirectly though measuring motor current in the mechanized drive unit used to apply force to the syringe plunger. Unfortunately, this method of measurement introduces a number of substantial inaccuracies arising from, for example, differences between motors, mechanical friction of the system, and frictional differences between syringes.

An alternate and more direct method of pressure measurement is the use of a load sensor to measure force within the mechanized drive unit. Although this method should eliminate inaccuracies arising from differences between motors and from mechanical drive friction, it will not eliminate inaccuracies arising from variation in frictional resistance within the syringe and variations in syringe diameter. Moreover, such frictional resistance is a complex function of a number of variables including the plunger speed, the pressure of the fluid, the degree of lubrication, the contact surface between the plunger cover and the syringe wall, the length of time the plunger has remained stationary, and the fluid that is being pressurized.

A more accurate method of fluid pressure measurement in a syringe injector system would be direct measurement thereof with a pressure transducer in contact with the pressurized injection fluid. This method also suffers from several substantial problems, however. Because sterility has to be maintained, the transducer must either be disposable or be connected through a flexible, sterilizable membrane to prevent cross contamination between patients. Under either method the transducer must be connected by the user and disconnected when finished. Further, there must be a cumbersome cable attachment to the transducer.

It is, therefore, very desirable to develop devices and methods for measuring pressure in a syringe injection system that reduce or eliminate some of the drawbacks associated with the devices and methods discussed above.

SUMMARY OF THE INVENTION

The present invention provides an injection system for injection of a fluid medium. In general, the injection system comprises:

a. a syringe including an elongated cylindrical body, the syringe further including a plunger having a contact surface, the contact surface contacting the fluid medium, the plunger being movably mounted in the cylindrical body for pressurizing the fluid medium; and b. a sensor to detect the force upon at least a portion of the contact surface during pressurization of the fluid medium, thereby enabling determination of a pressure of the fluid medium within the syringe.

The contact surface preferably comprises a first surface for contacting the fluid medium and a second surface, substantially opposite the first surface, which second surface does not contact the fluid medium. Preferably, at least the portion of the contact surface upon which the sensor detects the applied force is fabricated from a deformable material such as a flexible, elastomeric polymer.

In one embodiment, the sensor is in operative connection with at least a portion of the second surface of the contact surface such that force on that portion of the second surface is transmitted to the sensor during pressurization of the fluid medium. The sensor may be in direct contact with the second surface of the contact surface or in contact with the second surface via at least one intermediate member. The intermediate member may, for example, comprise a solid member in contact with the second surface at one end thereof and in contact with the sensor at the other end thereof. The intermediate member may also comprise a chamber filled with a fluid in operative connection with at least a portion of the second surface of the contact surface. Any increase in pressure in the syringe will cause an increase in the fluid pressure within the chamber. The sensor is in operative connection with the chamber to detect the pressure therein and thereby determine the fluid pressure within the syringe.

In another embodiment, the sensor detects movement of at least a portion of the contact surface during pressurization of the fluid medium. The force upon the portion of the contact surface is a function of, for example, the distance or amount of the movement of the portion of the contact surface. The pressure within the syringe can, therefore, be calculated from the movement of the portion of the contact surface.

In general, the syringe and plunger contact surface of the present invention are preferably removable from a powered injector for sterilization or disposable after use with a single patient. The sensor of the present invention is preferably separable from the syringe and plunger contact surface. Because the sensor is separable from the syringe and plunger contact surface and does not contact the injection medium, the sensor can be reused with another patient without the need for sterilization. In one embodiment of the present invention, for example, the injection system preferably further comprises an injector having a powered drive member adapted to form an operative connection with the plunger to move the plunger in the cylindrical body. Preferably, the sensor is attached to the powered drive member. The sensor remains attached to the powered drive member after the syringe and plunger are removed for sterilization or disposal.

The present invention also provides a method of sensing pressure in a syringe. As discussed above, the syringe comprises an elongated, cylindrical body and a plunger movably mounted in the cylindrical body for pressurizing the fluid medium. The plunger comprises a contact surface to contact the liquid medium. The method comprises the step of sensing force on at least a portion the contact surface during pressurization of the fluid medium.

The present invention also provides a device for measurement of pressure of an injection fluid within a syringe, the device comprises:

a. a plunger having a contact surface, the contact surface contacting the fluid medium, the plunger adapted to be movably mounted in the syringe for pressurizing the fluid medium; and b. a sensor to detect the force upon at least a portion of the contact surface during pressurization of the fluid medium, thereby enabling determination of a pressure of the fluid medium within the syringe.

The present invention provides for more accurate sensing of fluid pressure in a syringe injection system than via measurement of motor current or motor force. Moreover, the present invention provides such accuracy while avoiding direct contact of a pressure sensing device (for example, a transducer) with the fluid medium and the numerous problems associated therewith. Further, the present invention is easy and inexpensive to manufacture, and syringes currently in use can be relatively easily modified to practice the present invention.

DETAILED DESCRIPTION OF THE INVENTION

Figure 1:
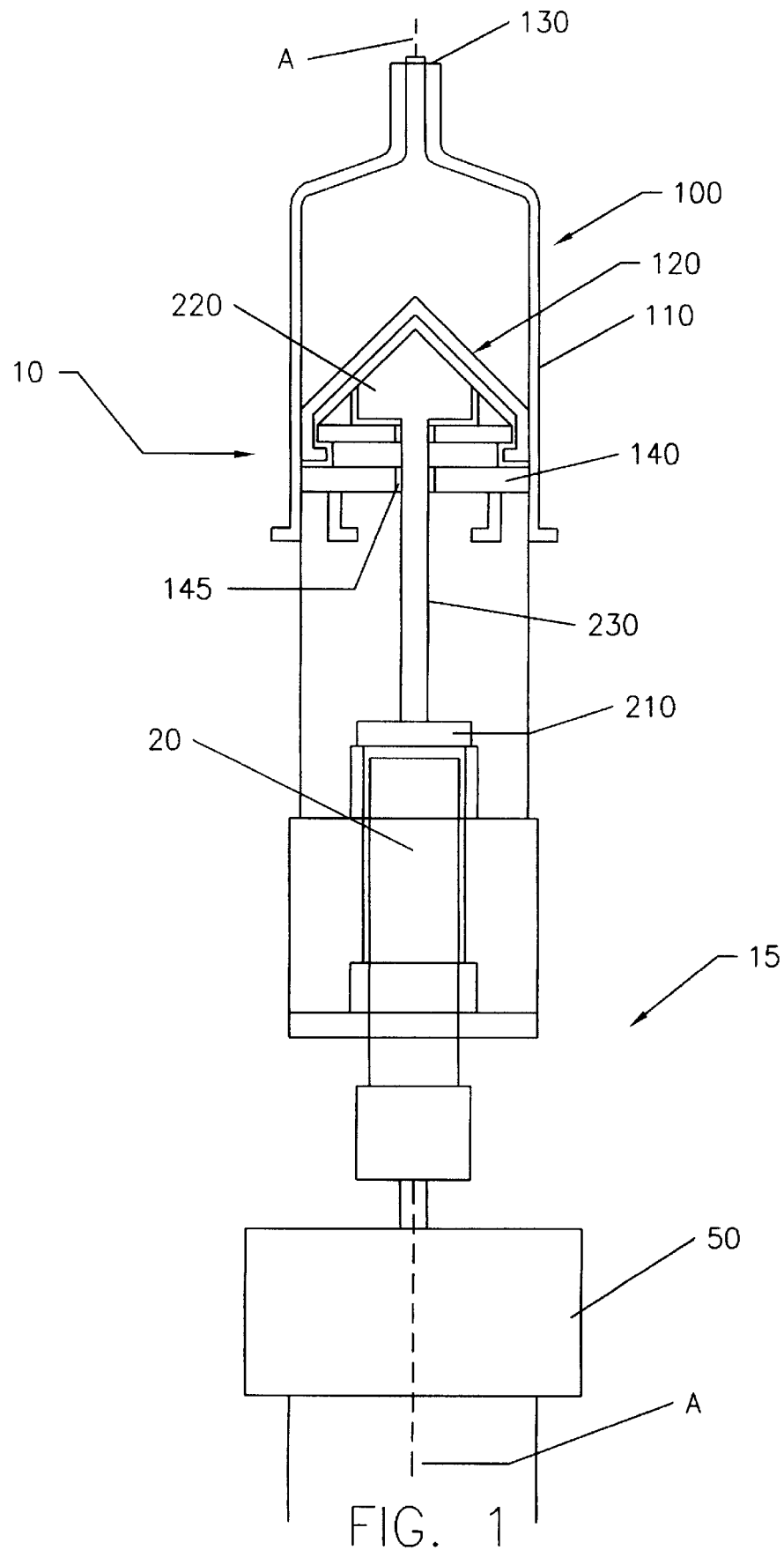
FIG. 1 illustrates a cross-sectional view of an embodiment of an injector syringe system of the present invention.
Figure 2:
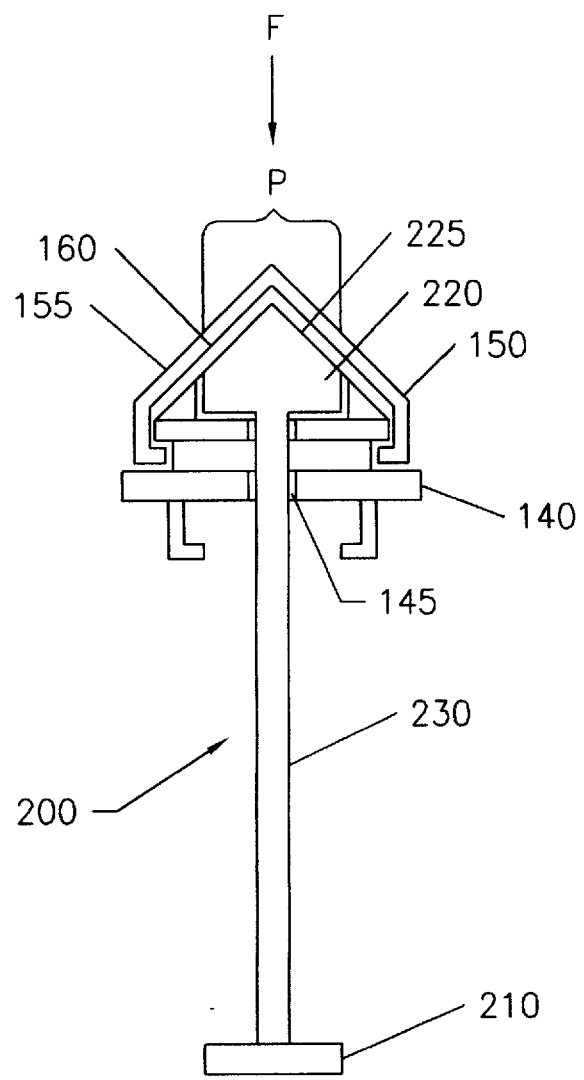
FIG. 2 illustrates a cross-sectional view of a plunger and an embodiment of a pressure measuring mechanism of the present invention.
Figure 3:
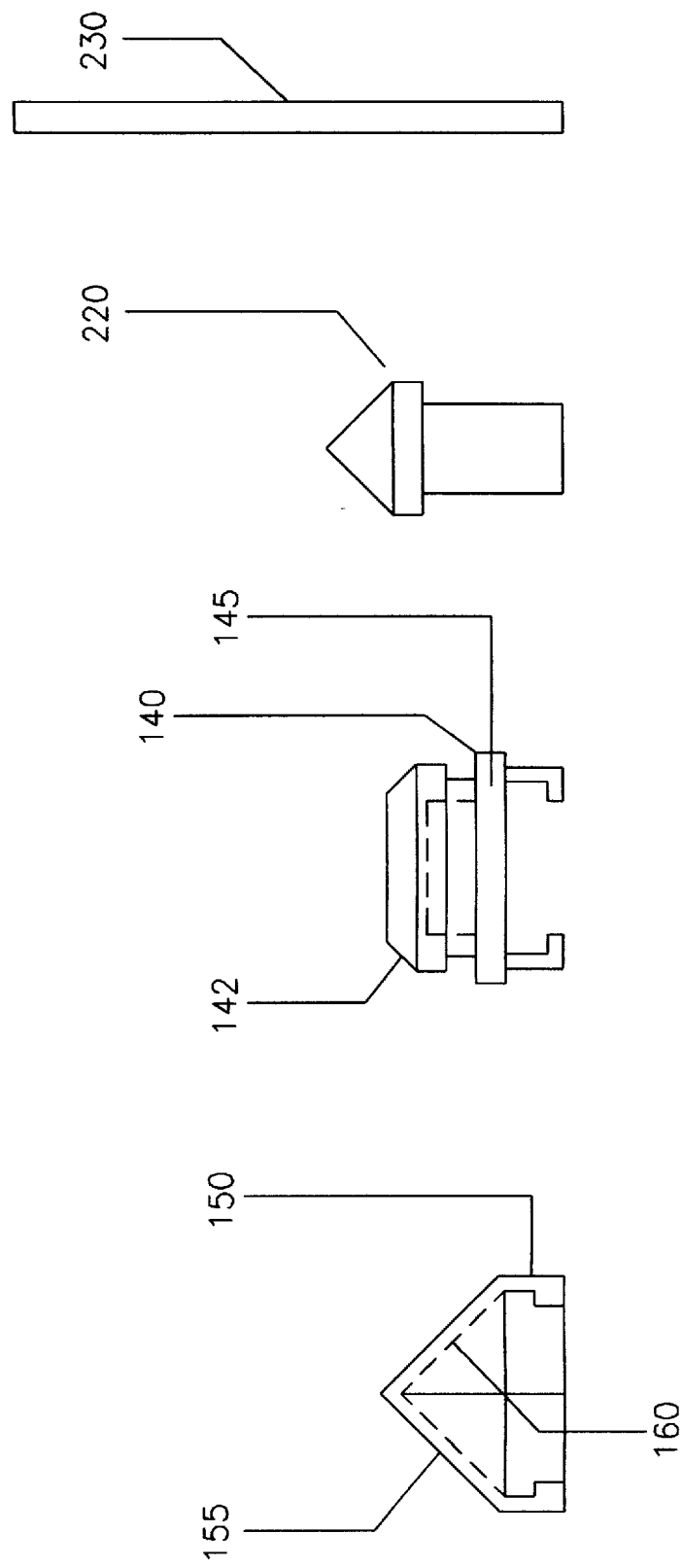
FIG. 3 illustrates the disassembled components of the plunger and the pressure measuring mechanism of the embodiment of FIG. 2.

FIGS. 1 through 3 illustrate an injection system 1 comprising a syringe system 10 and a mechanism 15 for providing a powered linear drive to pressurize a liquid medium. For example, drive mechanism 15 may comprise a powered injector including a piston 20 in powered connection with a gear motor 50 as known in the art.

Syringe 100 preferably comprises an elongated cylindrical body 110 and a plunger 120 that is slidably mounted in cylindrical body 110. Plunger 120 is in operative connection with piston 20 such that piston 20 can force plunger 120 substantially linearly forward toward tip 130 of syringe 100 to pressurize the liquid injection medium within cylindrical body 110.

As illustrated in FIGS. 2 and 3, plunger 120 preferably comprises a base 140 and a contact surface 150. Contact surface 150 comprises a first, outer surface 155 for contacting the fluid medium and a second, inner surface 160, substantially opposite first surface 155, which does not contact the fluid medium. Contact surface 150 preferably surrounds and is supported by a forward portion 142 of base 140. Second surface 160, which contacts the surface of forward portion 142 of base 140 is preferably formed in substantially the same shape as the surface of forward portion 142.

As used herein to describe injection system 1, the terms "axial" or "axially" refer generally to an axis A around which injection system 1 (including, for example, plunger 120 and syringe 100) is preferably formed (although not necessarily symmetrically therearound). The terms "proximal" or "forward" refer generally to an axial direction toward syringe tip 130 of syringe 100. The terms "distal" or "rearward" refer generally to an axial direction toward the end of injection system 1 opposite syringe tip 130. The term "radial" refers generally to a direction normal to axis A.

Syringe 100 further comprises a mechanism to measure the pressure of the liquid injection medium. The pressure measuring mechanism preferably comprises a sensor, such as a motion, force or pressure sensor, adapted to measure the force/pressure upon at least a portion of contact surface 150. The sensor may, for example, be in operative connection with second surface 160 via direct contact with second surface 160 or through one or more intermediate members. Such intermediate members can be solid, fluid or a combination thereof. The sensor can alternatively detect motion of at least a portion of contact surface 150 without any direct or indirect contact of the sensor with contact surface 150.

In the embodiment of FIGS. 1 through 3, a sensor 210 is in operative contact with second surface 160 via an intermediate plunger insert member 220 which is moveably positioned within a passage 145 in plunger base 140. The forward surface 225 of plunger insert member 220 preferably conforms substantially to the shape of that portion of second surface 160 to be contacted by a forward surface 225 of plunger insert member 220. The pressure measuring mechanism further comprises an intermediate load member 230 in contact at one end thereof with plunger insert member 220 and in contact at the other end thereof with sensor 210. Sensor 210 may, for example, comprise a load cell such as a HiTec Model HC-100 load cell. In the illustrated embodiment, load member 230 preferably passes through a bore or passage in piston 20 to contact sensor 210 which is positioned within piston 20.

In the embodiment illustrated in FIG. 1 through 3, a rearward force F on a portion P (see FIG. 2) of contact surface 150 is transferred to piston insert member 220. Because piston insert member 220 is moveably positioned within passage 145, piston insert member 220 exerts a rearward force on load member 230. The force on load member 230 is transmitted to sensor 210.

In this manner, the pressure of the fluid within cylindrical body 110 of syringe 100 can be measured. The force measured by sensor 210 is approximately equal to the area of contact surface 150 in contact with sensor 210 (for example, via plunger insert member 220) multiplied by the fluid pressure in syringe 100. In general, therefore, the larger the area of contact (that is, the larger the area of portion P), the grater accuracy that can be achieved.

At least portion P of contact surface 150 is fabricated from a deformable material, such as an flexible, elastomeric polymer. As common in the syringe injector arts, the entirety of contact surface 150 may be fabricated from an flexible, elastomeric material. The elasticity of such materials generally make them well suited for the transmission of force therethrough.

Because increased stiffness of contact surface 150 can adversely affect the pressure measurements, thinner (and consequently less stiff) elastomeric materials (at least in portion P) are preferred. Moreover, the effects of stretching arising from syringe side wall friction should be minimized. This can be accomplished, for example, (1) by ensuring that the perimeter of portion P is sufficiently distant from the radial sides of contact surface 150 which contact and form a seal with the inner wall of syringe 100, (2) by making radial sides portions of contact surface 150 less flexible and/or (3) by reducing friction between the radial sides of contact surface 150 and the inner wall of syringe 100.

Furthermore, plunger insert member 220 and load member 230 are preferably of a length to create a substantially flush contact with second surface 160 while minimizing force upon and deformation of contact surface 150 resulting from its contact with plunger insert member 220.

In one experiment, a plunger insert member having a conical forward surface with a base diameter of approximately 0.5 inch was used. This diameter was found to be large enough to achieve sufficient surface area (approximately 0.196 square inches), but was sufficiently distant from the radial sides of the contact surface to keep measurement distortions arising from compression and friction on the inner wall of cylindrical body 100 sufficiently small. With a contact area of 0.196 square inches at 450 psi., for example, there is a force of approximately 88.2 lbs. exerted on pressure insert member 220.

Figure 4A:
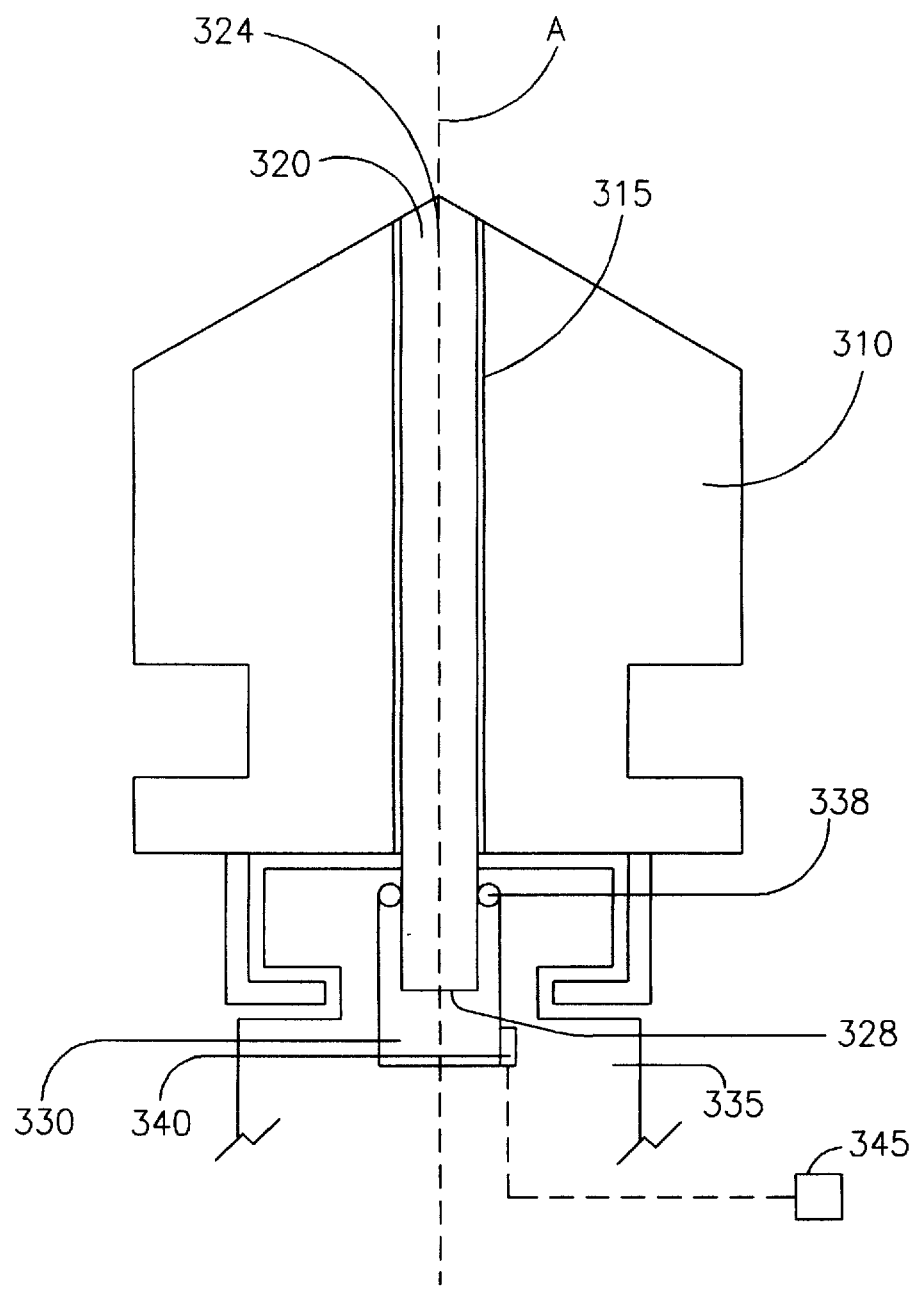
FIG. 4A illustrates a cross-sectional view of an embodiment of a pressure measuring mechanism of the present invention in which pressurization of the injection medium causes an increase in the pressure of a fluid in operative contact with the second surface of the contact surface.

In an alternative embodiment illustrated in FIG. 4A, a plunger 310 comprises a passage 315 therethrough in which a plunger insert member 320 is slidably disposed. A forward end 324 of plunger insert member 320 is in contact with the contact surface (not shown in FIG. 4A) as described above. A rearward end 328 of plunger insert member 320 is in contact with a fluid contained within a fluid reservoir 330 preferably formed in a drive piston 335. A sealing member such as an O-ring 338 preferably contacts the outer radial surface of plunger insert member 320 to substantially prevent leakage of the fluid from reservoir 330. The force upon the contact surface is transferred to the fluid within reservoir 330. The resulting pressure increase of the fluid in reservoir 330 can then be measured with a sensor 340, such as a pressure transducer, in contact with the fluid in reservoir 330. Sensor 340 may be connected to a data collection/control device comprising, for example, a processor 345 via leads as known in the art.

Figure 4B:
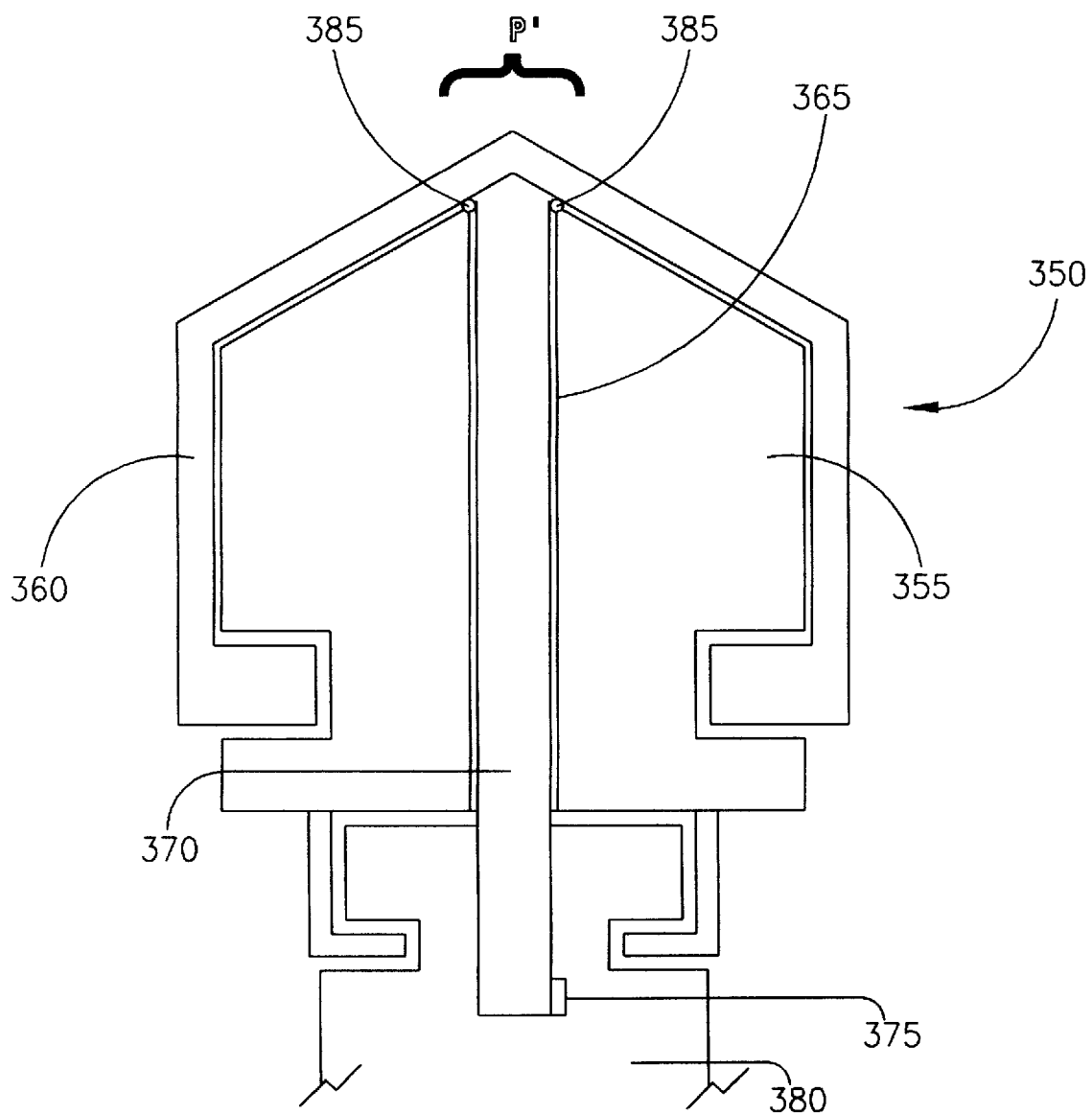
FIGS. 4B and 4C illustrate a cross-sectional view of an embodiment of a pressure measuring mechanism of the present invention in which pressurization of the injection medium causes an increase in the pressure of a fluid in direct contact with the second surface of the contact surface.
Figure 4C:
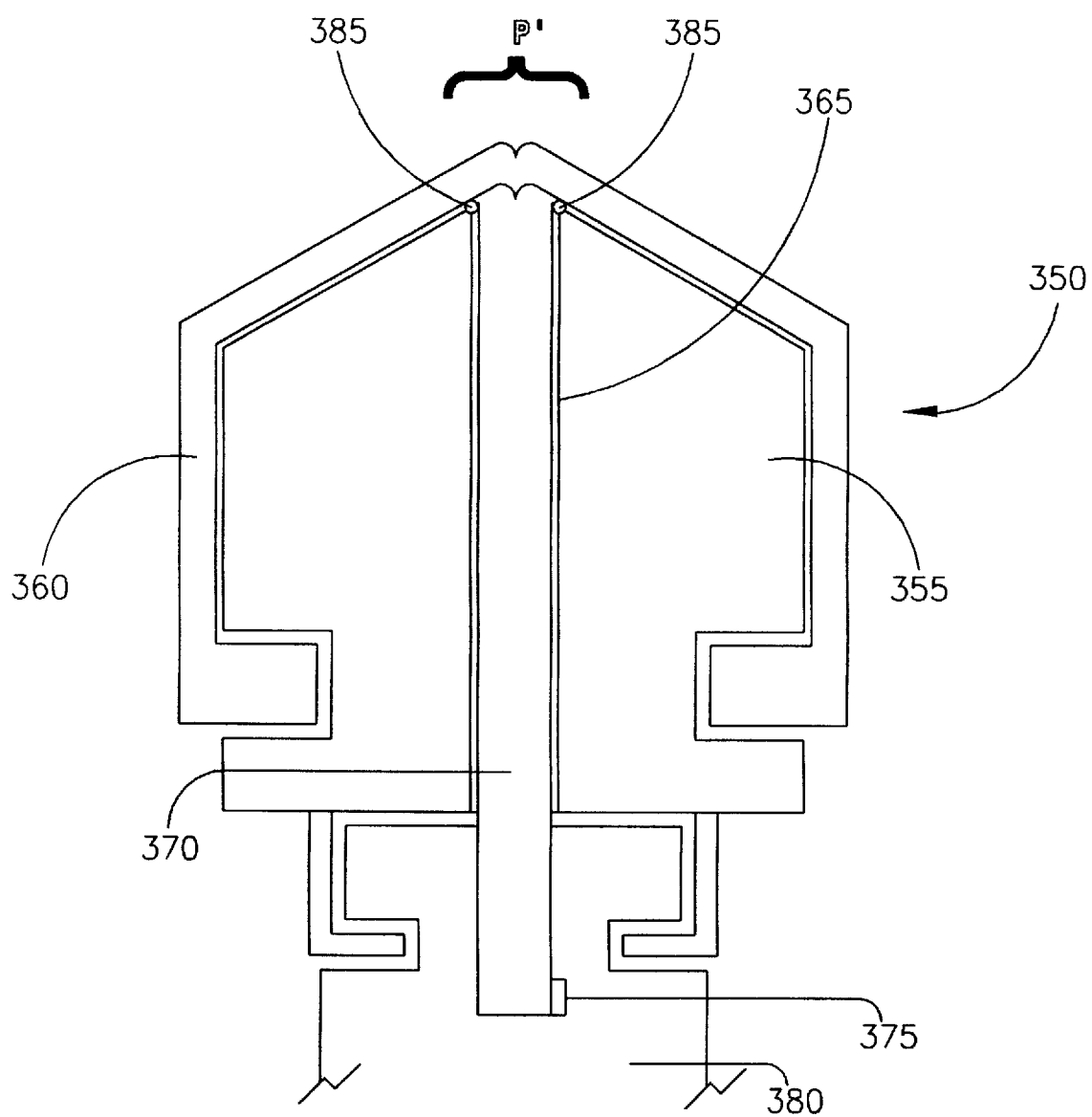

In another embodiment illustrated in FIGS. 4B and 4C, a plunger 350 comprises a plunger base 355 and a contact surface 360. Plunger base 355 preferably comprises a passage 365 therethrough. A fluid-filled chamber 370 is preferably disposed within passage 365 to be in communicative connection with a portion P' of contact surface 360 (substantially defined by the forward opening of passage 365). As fluid pressure within the syringe (not shown) is increased, portion P' of contact surface 360 is deformed as shown in FIG. 4C. This deformation of portion P' causes the pressure of the fluid (preferably air) within chamber 370 to increase proportionately to the increase of fluid pressure within the syringe. The pressure of the fluid within chamber 370 is monitored with a sensor 375. Preferably, chamber 370 is attached to drive piston 380. Sealing member, such as O-ring 385, is preferably provided to prevent leakage of fluid during pressurization of the syringe.

Figure 5:
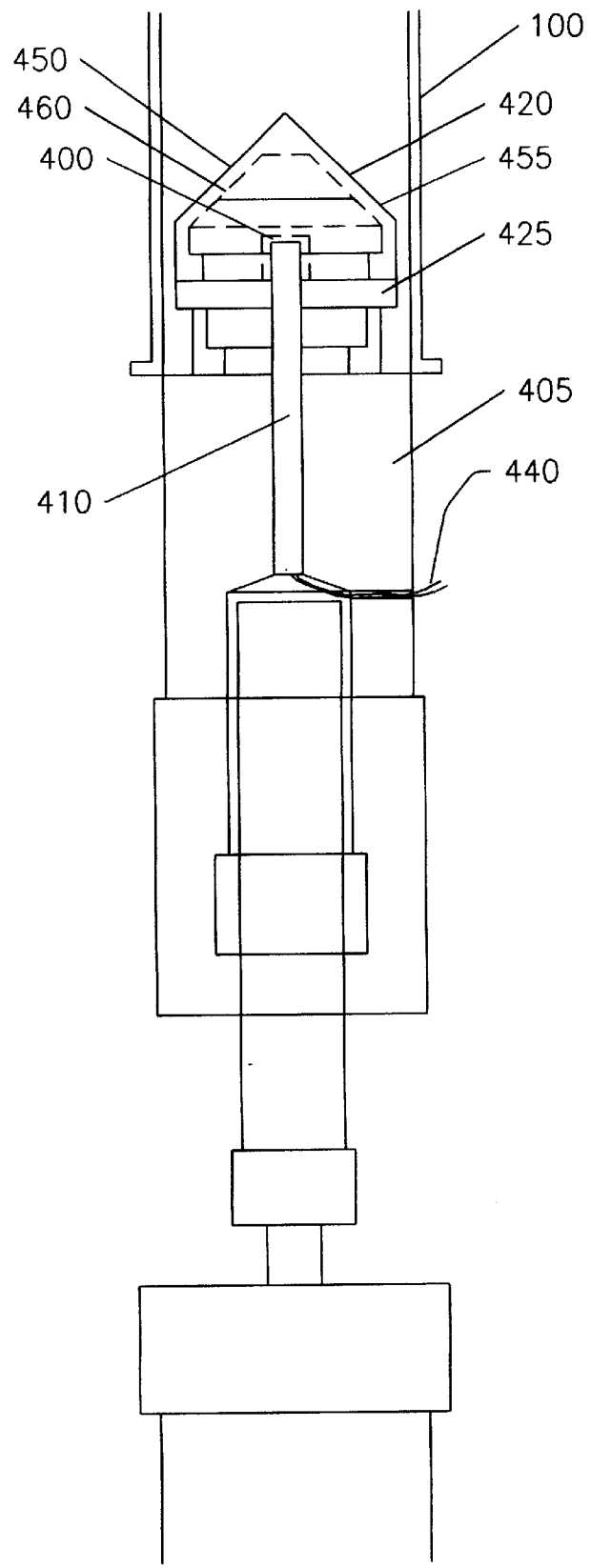
FIG. 5 illustrates a cross-sectional view of another embodiment of an injector syringe system of the present invention.
Figure 6:
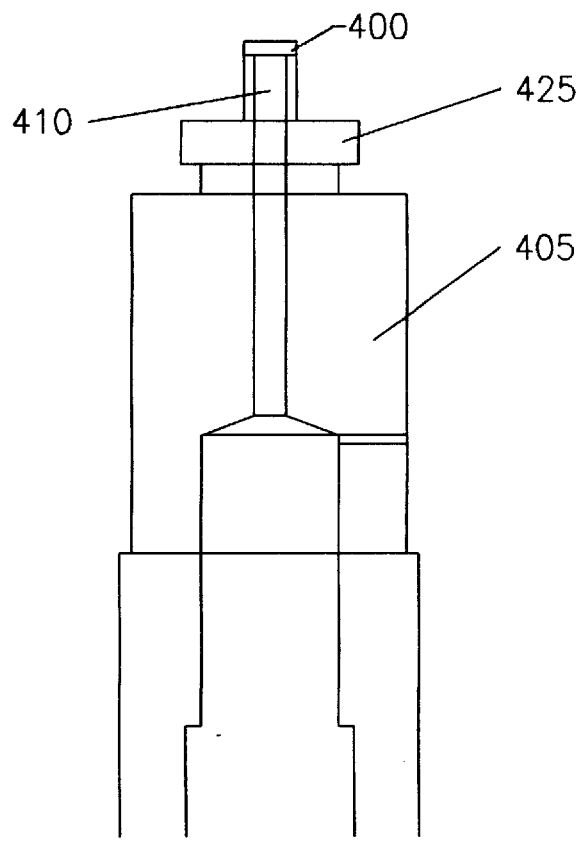
FIG. 6 illustrates a cross-sectional view of the piston and pressure sensor assembly of the embodiment of FIG. 5.
Figure 7:
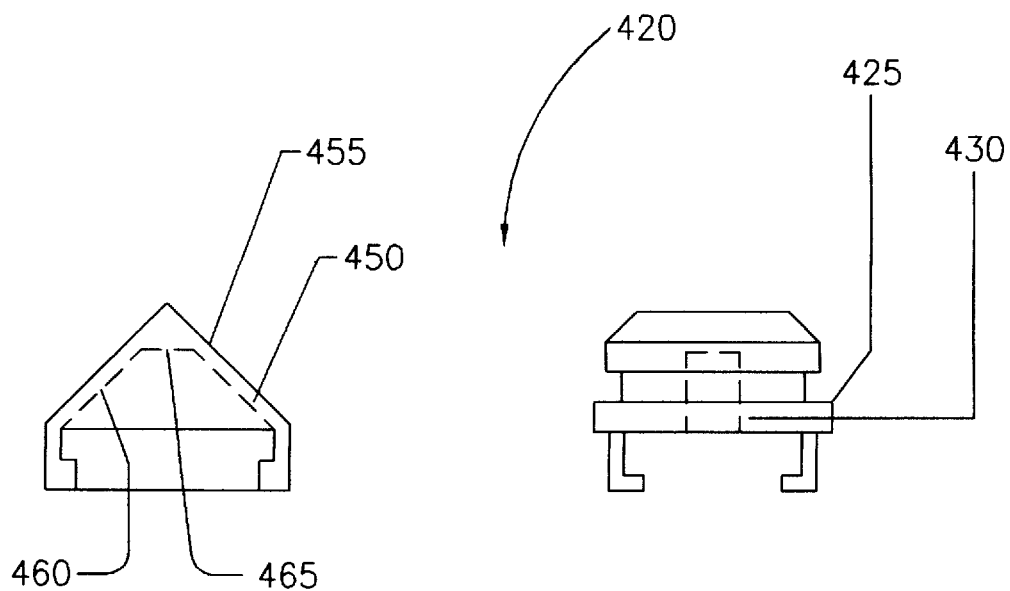
FIG. 7 illustrates the disassembled components of the plunger of the embodiment of FIG. 5.

FIGS. 5 through 7 illustrate another embodiment of the present invention in which the contact surface of the plunger is in substantially direct connection with a sensor to measure pressure. In this design, a miniature pressure transducer 400 is preferably mounted on a piston tip extension 410 of piston 405. Plunger 420, as described above, preferably comprises a base member 425 and an elastomeric contact surface 450. Contact surface 450 comprises a first or outer surface 455 and a second or inner surface 460. Plunger base member 425 has an access passage 430 therethrough such that when syringe 100 is installed to the injector head (not shown), the second or inner surface 460 of contact surface 450 contacts transducer 400. Pressure is transmitted through contact surface 450 to transducer 400. Contact surface 450 is preferably fabricated to form a substantially flat portion 465 on second surface 460 to provide good contact with transducer 400. Contact surface 450 is preferably fabricated as thin as possible (at least in the area through which force is transmitted to transducer 400) to maximize the efficiency of such force transfer. Pressure transducer 400 is connected to a data collection/control device comprising, for example, a computer processor (not shown) via leads 440 as known in the art.

Figure 8A:
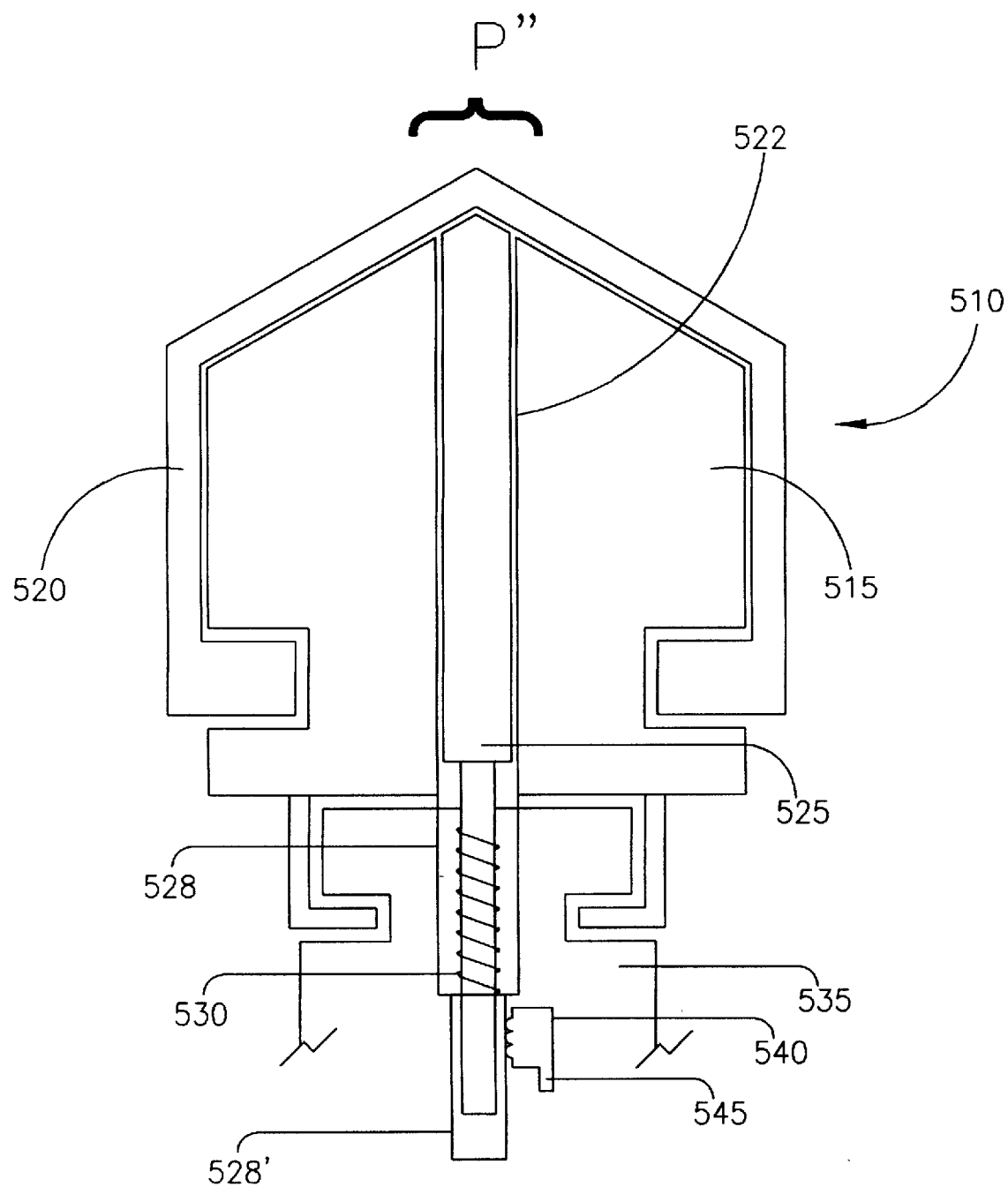
FIGS. 8A and 8B illustrate a cross-sectional view of an embodiment of a pressure measuring mechanism of the present invention in which pressurization of the injection medium causes a measurable deformation of the contact surface of the plunger.
Figure 8B:
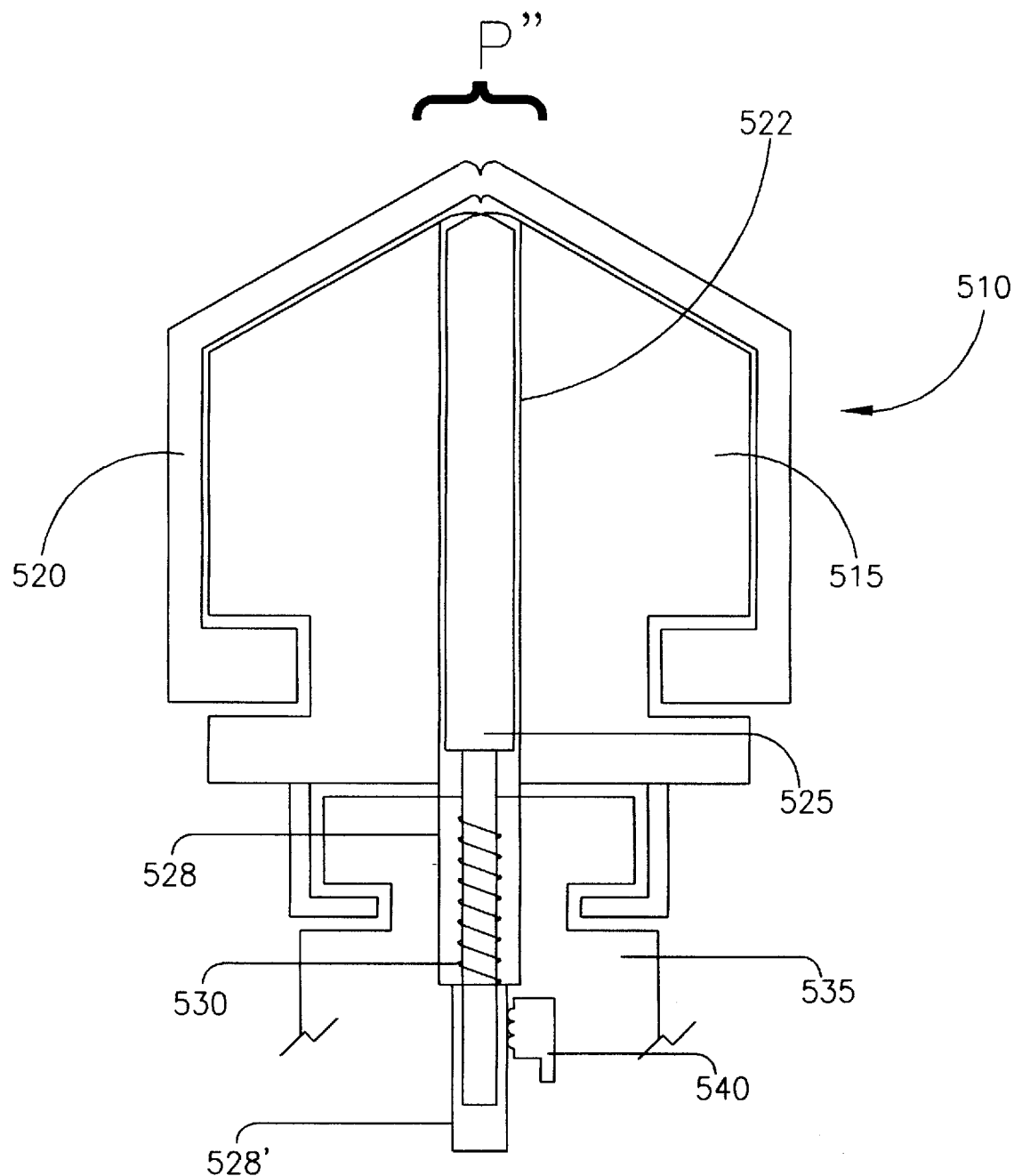

FIGS. 8A and 8B illustrate a further embodiment of the present invention comprising a plunger 510. Plunger 510 preferably comprises a base 515 and a contact surface 520. Plunger base 510 preferably comprises a passage 522 therethrough. A sensing member 525 is disposed within passage 522 to be in operative contact with a portion P''' of contact surface 520. Sensing member 525 is preferably biased forward, for example, via a spring 530. As fluid pressure within the syringe (not shown) is increased, portion P''' of contact surface 520 is deformed as shown in FIG. 8B. This deformation of portion P''' causes sensing member 525 to move rearward though passages 522 and passages 528 and 528' in drive piston 535. The movement of sensing member 525 is monitored with a sensor 540 preferably disposed within drive piston 535. Because the degree of movement of sensing member 525 is a function of the pressure of the fluid medium within the syringe (not shown in FIGS. 8A and 8B), the pressure of the fluid medium can be determined therefrom. Sensor 540 is preferably connected to a data collection and/or control device via wires 545.

Although the present invention has been described in detail in connection with the above examples, it is to be understood that such detail is solely for that purpose and that variations can be made by those skilled in the art without departing from the spirit of the invention except as it may be limited by the following claims.

What is claimed is:

1. An injection system for injection of a fluid medium, the injection system comprising:

a. a syringe comprising an elongated cylindrical body and a plunger having a contact surface, the contact surface comprising a first surface that contacts the fluid medium and a second surface, substantially opposite the first surface, that does not contact the fluid medium, the plunger being movably mounted in the cylindrical body for pressurizing the fluid medium; and b. a sensor for detecting a force upon at least a portion of the contact surface during pressurization of the fluid medium, thereby enabling determination of a pressure of the fluid medium within the syringe, the sensor being in operative connection with at least a portion of the second surface of the contact surface such that force on the at least a portion of the second surface is transmitted to the sensor during pressurization of the fluid medium.

2. The injection system of claim 1 wherein the sensor is in direct contact with the at least a portion of the second surface of the contact surface.

3. The injection system of claim 1 wherein the contact with the at least a portion of the second surface of the contact surface is via at least one intermediate member.

4. The injection system of claim 1 wherein the sensor is a load cell.

5. The injection system of claim 1 wherein the sensor detects movement of the at least a portion of the contact surface during pressurization of the fluid medium, the force upon the at least a portion of the contact surface being a function of the displacement of the at least a portion of the contact surface.

6. The injection system of claim 3 wherein the intermediate member comprises a chamber filled with a fluid in operative connection with the at least a portion of the second surface of the contact surface, an increase in pressure in the syringe causing an increase in the fluid pressure within the chamber, the sensor being in operative connection with the chamber to detect the pressure therein.

7. The injection system of claim 1 further comprising an injector, the injector having a powered drive member adapted to form an operative connection with the plunger to move the plunger in the cylindrical body, the sensor being attached to the powered drive member.

8. The injection system of claim 1 wherein the at least a portion of the contact surface is fabricated from a flexible material.

9. The injection system of claim 3 wherein the at least one intermediate member comprises a substantially solid member in operative connection with the at least a portion of the second surface of the contact surface.

10. The injection system of claim 9 wherein the at least one intermediate member is biased against the at least a portion of the second surface of the contact surface.

11. The injection system of claim 10 wherein the at least one intermediate member is biased by a spring.

12. The injection system of claim 6 wherein the fluid comprises air.

13. A method of sensing fluid pressure, comprising the following steps: providing a syringe comprising an elongated, cylindrical body and a plunger having a contact surface, the contact surface comprising a first surface that contacts the fluid and a second surface, substantially opposite the first surface, that does not contact the fluid, the plunger being movably mounted in the cylindrical body for pressurizing the fluid; providing a sensor for detecting a force upon at least a portion of the contact surface during pressurization of the fluid, thereby enabling determination of a pressure of the fluid within the syringe, the sensor being in operative connection with at least a portion of the second surface of the contact surface such that force on the at least a portion of the second surface is transmitted to the sensor during pressurization of the fluid; and sensing force on at least a portion of the contact surface during pressurization of the fluid.

14. The method of claim 13 wherein the sensor is in direct contact with the at least a portion of the second surface of the contact surface.

15. The method of claim 13 wherein the contact with the at least a portion of the second surface of the contact surface is via at least one intermediate member.

16. The method of claim 13 wherein the step of sensing comprises detecting movement of the at least a portion of the contact surface during pressurization of the fluid, the force upon the at least a portion of the contact surface being a function of the displacement of the at least a portion of the contact surface.

17. A device for measurement of pressure of an injection fluid within a syringe, the device comprising:
   a. a plunger comprising a contact surface having a first surface that contacts the fluid and a second surface, substantially opposite the first surface, that does not contact the fluid, the plunger adapted to be movably mounted in the syringe for pressurizing the fluid medium; and
   b. a sensor for detecting the force upon at least a portion of the contact surface during pressurization of the fluid medium, thereby enabling determination of a pressure of the fluid medium within the syringe, the sensor being in operative connection with at least a portion of the second surface of the contact surface such that force on the at least a portion of the second surface is transmitted to the sensor during pressurization of the fluid medium.

18. The device of claim 17 wherein the sensor is in direct contact with the at least a portion of the second surface of the contact surface.

19. The device of claim 17 wherein the contact with the at least a portion of the second surface of the contact surface is via at least one intermediate member.

* * * * *